United States Patent [19]
Fredricks

[11] Patent Number: 5,327,772
[45] Date of Patent: Jul. 12, 1994

[54] STEAM QUALITY SENSOR

[76] Inventor: William C. Fredricks, 325 Stony Hill Rd., Quarryville, Pa. 17566

[21] Appl. No.: 26,533

[22] Filed: Mar. 4, 1993

[51] Int. Cl.$^5$ ............................ G01N 25/60; G01K 17/00
[52] U.S. Cl. ................................. 73/25.04; 73/29.01; 374/40; 374/42
[58] Field of Search ............... 73/25.01, 25.04, 29.01, 73/29.03, 29.05, 861.04; 374/16, 24, 25, 27, 33, 42, 40

[56] References Cited

U.S. PATENT DOCUMENTS

| | | | |
|---|---|---|---|
| 4,028,942 | 6/1977 | Gardiner | 73/29.01 |
| 4,034,597 | 7/1977 | Fredriksson | 73/29 |
| 4,149,403 | 4/1979 | Muldary et al. | 73/29 |
| 4,295,368 | 10/1981 | Jannone | 374/42 |
| 4,402,183 | 9/1983 | Dimitroff et al. | 60/660 |
| 4,471,620 | 9/1984 | Binstock et al. | 60/653 |
| 4,561,785 | 12/1985 | Long et al. | 374/33 |
| 4,574,622 | 3/1986 | Kaya et al. | 73/112 |
| 4,576,036 | 3/1986 | Huang et al. | 73/29.01 |
| 4,776,301 | 10/1988 | Dziubakowski | 122/479 |
| 4,827,429 | 5/1989 | Silvestri, Jr. | 364/494 |
| 4,833,688 | 5/1989 | Smith | 374/42 |
| 4,891,948 | 1/1990 | Kure-Jensen et al. | 60/645 |
| 4,932,788 | 6/1990 | Yeh | 374/42 |
| 4,969,084 | 11/1990 | Smith | 364/165 |

Primary Examiner—Hezron E. Williams
Assistant Examiner—Michael Brock

[57] ABSTRACT

A method and apparatus are disclosed for determining steam quality wherein heat is added to or removed from a sample flow of steam to reach a point of superheating or subcooling. The amount of energy required to superheat or subcool the sample is factored in with other parameters such as steam flow rate, temperature and pressure to determine the quality of the steam. The steam quality sensor has many applications in equipment such as turbines, heat exchangers, condensers and the like.

18 Claims, 2 Drawing Sheets

STEAM QUALITY SENSOR

BACKGROUND OF THE INVENTION

The present invention relates to the measurement of steam quality. In particular, the invention relates to a method and apparatus for determining steam quality which involves adding heat to or removing heat from a sample of steam to obtain a divergence in pressure or temperature that occurs when the sample is superheated or subcooled.

The quality of a two-phase flow is a parameter of importance in the operation and design of heat exchangers, turbines, steam engines, pumps, piping systems and the like. In heat exchangers that operate at saturated conditions such as steam generators and condensers, performance is characterized by the state of fluid entering and leaving the heat exchanger. In order to determine the state of the fluid at saturation conditions, the inlet or exit quality must be known. In steam generators, for example, lower than expected outlet quality is an indication of poor heat transfer performance of the steam separation equipment. In turbines, high moisture content at the turbine inlet can cause turbine blade erosion as well as reduced steam efficiency.

Several techniques have been used to measure the quality of steam. One such technique is disclosed in U.S. Pat. No. 4,034,597 to Fredriksson in which a sample of steam is introduced into a variable-volume sampling chamber that is kept at constant temperature. The chamber is placed in the path of the steam flow to be sampled. After a sample of steam is introduced into the chamber, the chamber is closed and maintained at a constant temperature by allowing steam to flow past the chamber. The volume of the chamber is then increased and pressure is monitored to sense a drop in pressure that occurs once the entire liquid portion of the sample has evaporated.

U.S. Pat. No. 4,833,688 to Smith discloses a device for measuring steam quality that incorporates an evacuated sample chamber into which steam is drawn until the pressure within the chamber equals that within the steam flow. The device operates on the principal that a two-phase mixture, when throttled into a closed tank, will become superheated. The internal energy and enthalpy of the superheated mixture can be determined based on pressure and temperature measurements, which then allows the quality of the mixture to be computed. Before the steam sample is taken, the sample tank is preferably maintained at the same temperature as the source steam by using a heating element. Once the sample is taken, the tank is not heated by an external source.

U.S. Pat. No. 4,149,403 to Muldary et al discloses a device for measuring steam quality that incorporates sensors for measuring pressure in an unrestricted portion of the steam flow in comparison to pressure in a restricted, critical flow portion. The enthalpy of the steam is determined from experimentally generated curves which then allows for the calculation of steam quality.

U.S. Pat. No. 4,574,626 to Kaya et al discloses a method for measuring the enthalpy of a two-phase substance. Temperature, pressure and density measurements of the substance are made and tables are used to calculate the enthalpy of the substance.

U.S. Pat. No. 4,969,084 to Smith discloses a method for calculating the enthalpy of steam based on pressure, temperature and flow measurements.

U.S. Pat. No. 4,891,948 to Kure-Jensen et al discloses a steam turbine thermal performance monitor in which enthalpy is calculated based on various temperature and pressure measurements.

U.S. Pat. No. 4,471,620 to Binstock et al discloses a turbine low pressure bypass spray valve control system in which enthalpy is calculated based on temperature, pressure and flow measurements. The amount of cooling water necessary for injection into the steam flow is then determined.

U.S. Pat. No. 4,827,429 to Silvestri, Jr. discloses a method for determining turbine impulse chamber temperature which includes the calculation of enthalpy and entropy values based on various steam pressure and temperature measurements.

U.S. Pat. No. 4,776,301 to Dziubakowski discloses a method of controlling steam temperature that involves the measurement of flow, temperature and pressure to maintain a constant enthalpy of steam entering and leaving a superheater.

U.S. Pat. No. 4,402,183 to Dimitroff et al. discloses a pressure flash tank in which steam pressure is maintained at a constant level with varying amounts of input water flow and enthalpy values. The system includes the use of pressure transducers at various locations.

The present invention has been developed in view of the foregoing and to overcome the deficiencies of the prior art.

SUMMARY OF THE INVENTION

An object of the present invention is to provide a novel method and apparatus for measuring steam quality.

Another object of the present invention is to provide a method and apparatus for measuring steam quality that involves heating or cooling a sample of steam to obtain a divergence in pressure or temperature that results when the sample is superheated or subcooled. The amount of energy required to superheat or subcool the sample and the rate of flow of the sample are measured in order to determine steam quality.

These and other objects of the present invention will become more readily apparent from the following description.

DETAILED DESCRIPTION OF THE PREFERRED EMBODIMENTS

Figure 1A:
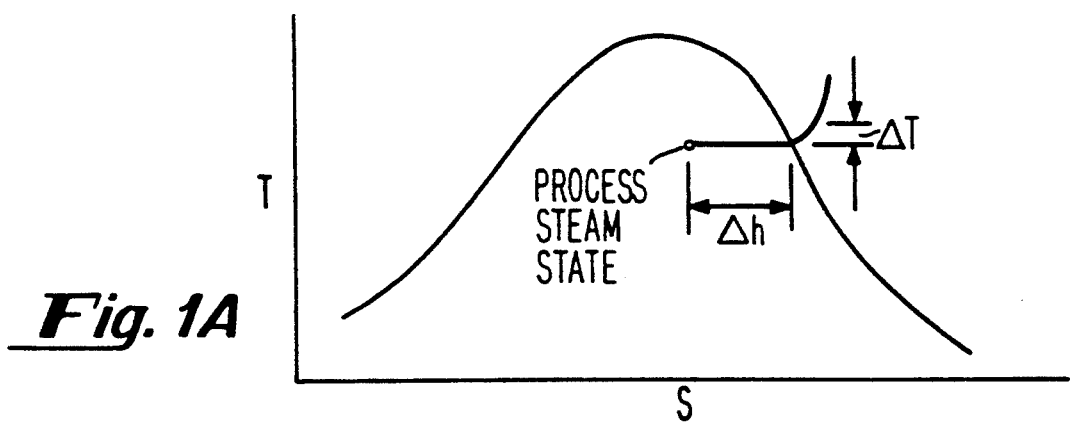
FIG. 1A is a graph of entropy versus temperature for a two-phase water mixture illustrating the change in temperature that occurs when the mixture is superheated.

The present invention provides a method and apparatus for measuring steam quality. As used herein, the term "steam quality" is defined as the ratio of the mass of water vapor to the total mass of water vapor and liquid of a steam sample. Thus, a steam quality of 0% would be pure liquid, while a quality of 100% would be pure vapor. The present invention takes advantage of the fact that a two-phase water mixture, when heated or cooled, will undergo a change in temperature and pressure once the point of superheating or subcooling is reached. FIGS. 1A-1D illustrate this point. In FIG. 1A, a sample of steam of given quality is heated until a divergence in temperature is achieved. This divergence in temperature indicates that the sample has become superheated. As more fully described below, by calculating the amount of energy required to heat the steam sample to the point of superheating, the quality of the steam can be determined.

Figure 1B:
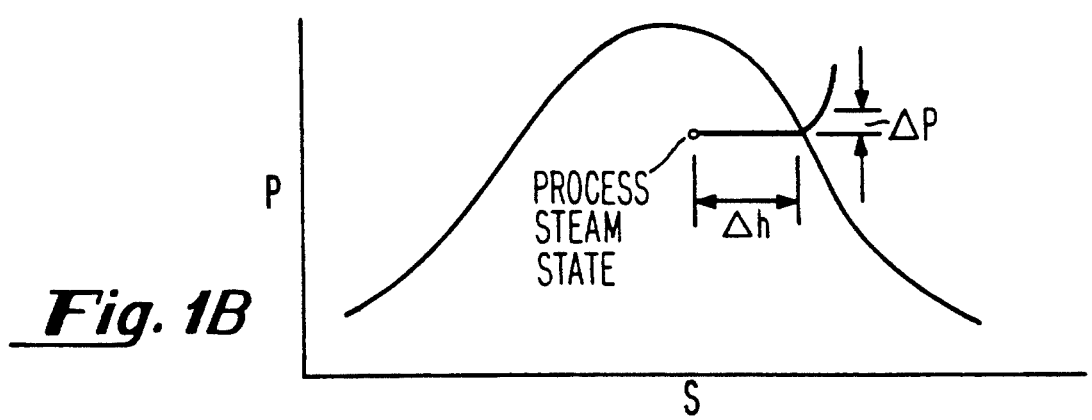
FIG. 1B is a graph of entropy versus pressure for a two-phase water mixture showing the change in pressure that occurs when the mixture is superheated.

Likewise, in FIG. 1B, a sample of steam of given quality is heated to a point at which a change in pressure occurs. This change in pressure indicates that the sample has become superheated, i.e., has reached a quality of 100%. The amount of energy required to heat the sample to the point of superheating can be used to determine the quality of the steam sample.

Figure 1C:
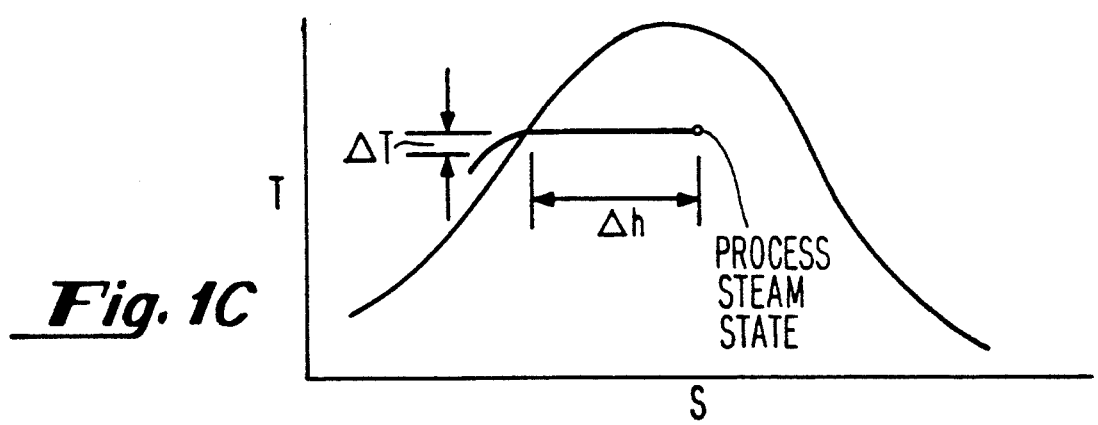
FIG. 1C is a graph of entropy versus temperature for a two-phase water mixture illustrating the change in temperature that occurs when the mixture is subcooled.
Figure 1D:
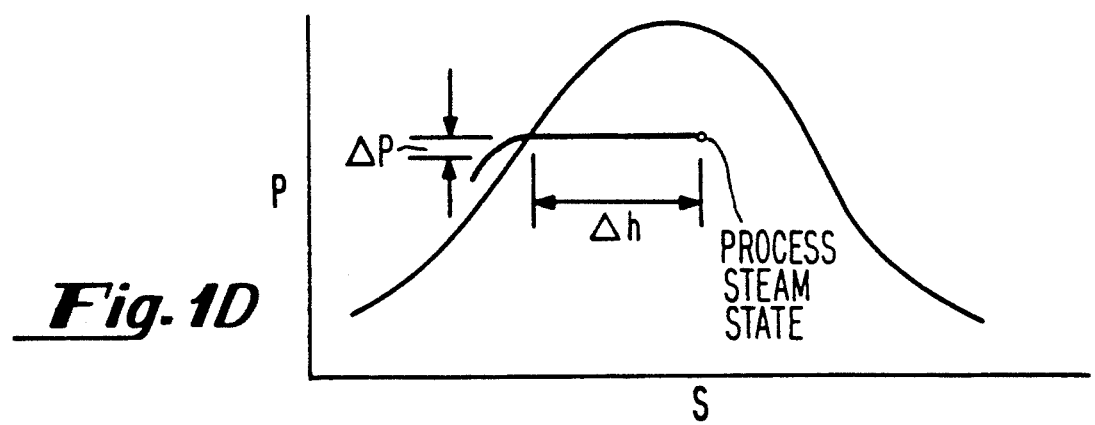
FIG. 1D is a graph of entropy versus pressure for a two-phase water mixture showing the change in pressure that occurs when the mixture is subcooled.

FIGS. 1C and 1D illustrate the changes in temperature and pressure that occur when a two-phase water mixture is subcooled. In FIG. 1C, a change in temperature occurs once heat is removed from a sample of steam to a point of subcooling, i.e., a quality of 0%. Similarly in FIG. 1D, a change in pressure results when a sample of steam reaches the point of subcooling. In each case, the amount of energy required to reach the point of subcooling is used to determine the quality of the steam sample.

Figure 2A:
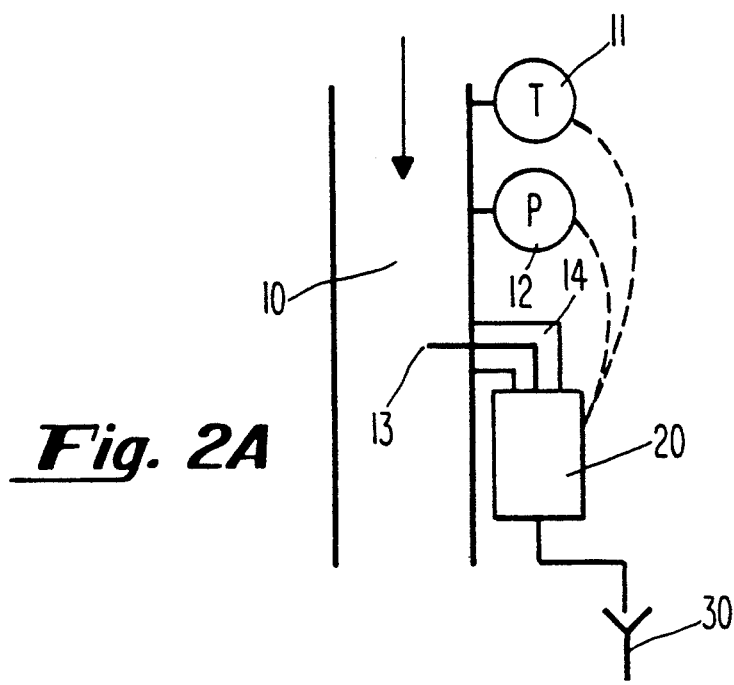
FIG. 2A is a schematic diagram of a steam quality sensing apparatus of the present invention.

A steam quality sensor of the present invention is schematically illustrated in FIG. 2A. A flow of process steam is established within the pipe 10. The temperature and pressure of the process steam are measured by a temperature sensor 11 and a pressure sensor 12. A sample pipe 13 penetrates the process steam pipe 10 and preferably extends to approximately the middle of the flow stream. The sample pipe 13 is insulated by an insulating layer 14. Steam drawn into the sample pipe 13 enters the steam quality sensor 20. A drain 30 is provided for collecting water that has passed through the steam quality sensor 20.

Figure 2B:
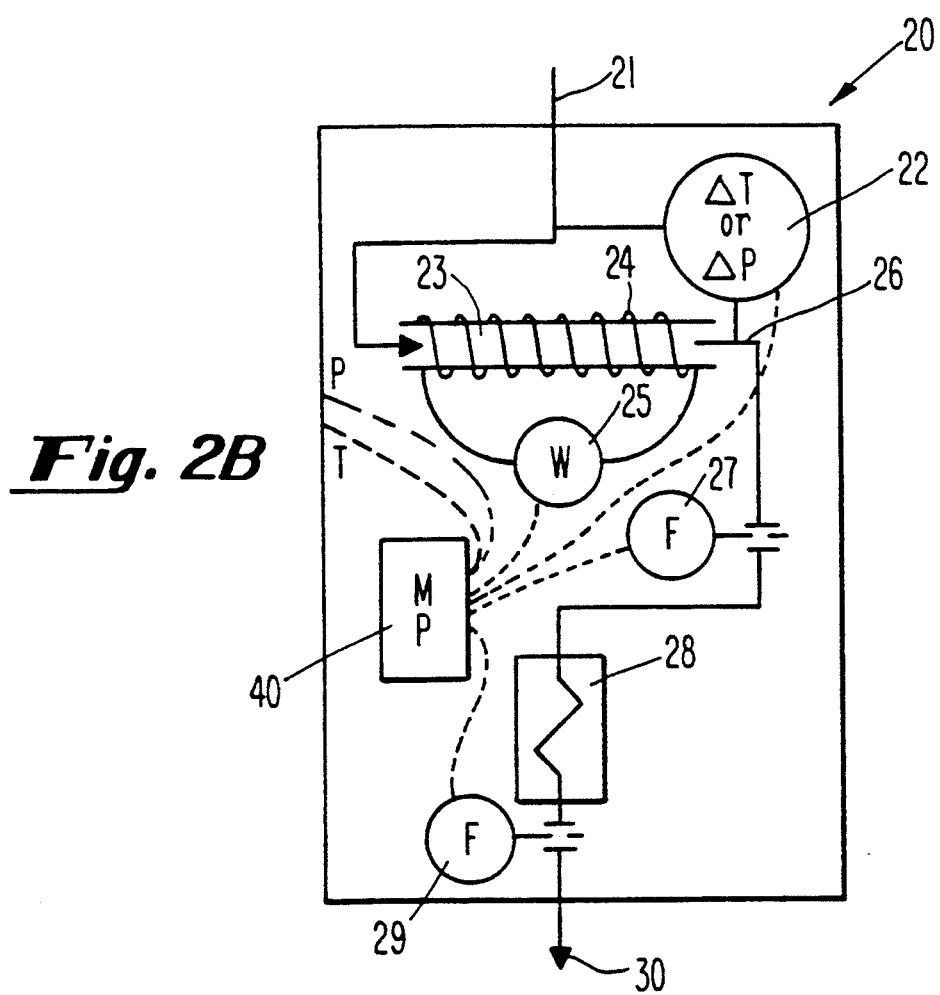
FIG. 2B is an enlarged schematic diagram of a steam quality sensor of the present invention.

FIG. 2B is an enlarged schematic diagram of the steam quality sensor 20 of the present invention. Sampled steam enters the steam quality sensor 20 through the inlet 21. The temperature and/or pressure of the steam is measured at the inlet 21 by the differential temperature or pressure sensor 22. The steam flows through chamber 23, which is of known volume. Steam within the chamber 23 is either heated or cooled by the element 24. The amount of heat added to or removed from the chamber 23 is measured by the wattmeter 25. Heating of the steam within the chamber 23 may be achieved by means such as an electrical heating coil, while cooling may be achieved by means such as a thermocouple with reversed polarity. Steam exits the chamber 23 via the exit pipe 26. At the exit pipe 26, the temperature and/or pressure of the steam is measured by the differential temperature or pressure sensor 22 to determine the point at which a difference in temperature and/or pressure is reached between the steam in the inlet 21 and the exit pipe 26. A first flow meter 27 is located at the exit pipe 26 for measuring the rate of steam flow. A condenser 28 is provided downstream from the first flow meter 27. A second flow meter 29 is provided downstream from the condenser 28 for measuring condensate flow. The pressure difference between the process steam flowing in the pipe 10 and the condensing chamber of the condenser 28 provides the motive force for establishing steam flow through the steam quality sensor 20. A drain 30 is provided for discharging the water after it has passed through the steam quality sensor. A microprocessor 40 collects inputs from the process steam temperature sensor 11, the pressure sensor 12, the wattmeter 25, the differential temperature and/or pressure sensor 22, and the first and second flow meters 27 and 28.

Steam quality is calculated by the microprocessor 40 and is determined in part by the amount of heat added to or removed from the steam flowing in the chamber 23 to produce superheating or subcooling. The point at which a change in pressure and/or temperature of the sample steam is reached and the rate of steam flow through the chamber 23 are input to the microprocessor 40. The steam flow through the chamber 23 is determined by the first steam flow sensor 27 and verified by the second condensate flow sensor 29. the quality of steam is calculated by the following equations:

$$x = 1 - (\Delta h/h_{fg}) \quad \text{(heating mode)}$$
$$x = \Delta h/h_{fg} \quad \text{(cooling mode)}$$

In the above equations, x is steam quality, $h_{fg}$ is a function of sample steam inlet temperature or pressure that is calculated in a known manner from steam tables or curves, and $\Delta h$ is equal to $Q/W_s$, wherein Q is heat input or subtraction and $W_s$ is mass flow of the steam sample. For electrical heating or cooling devices, heat input or subtraction (Q) is equal to current times voltage (I·V). For thermal heating or cooling devices, heat input or subtraction (Q) is equal to the mass flow of the heating or cooling fluid multiplied by the specific heat of the fluid multiplied by the differential temperature of the inlet and outlet fluid ($W_f \cdot C_p \cdot \Delta T_f$).

Steam flow through the chamber 23 is preferably kept at a constant rate. This is achieved by providing the condenser 28 with a cooling medium control that adjusts to maintain constant steam flow, i.e., the condenser pressure is varied thus changing the motive force to accommodate constant steam flow. When steam flow is kept constant, greater repeatability, sensitivity and accuracy are provided.

In the cooling mode of the present invention, heat is removed from the chamber 23 until a deviation in pressure or temperature is sensed, indicating the onset of subcooling. The amount of heat extracted from the steam flowing through the chamber 23 is then input into the microprocessor 40, along with the other pressure, temperature and flow inputs. The microprocessor 40 then calculates steam quality in accordance with the equations noted above. In the subcooling mode, the slightly subcooled liquid is preferably further subcooled by a heat exchanger to achieve a less hostile and more accurate measure of the condensate flow.

In the heating mode of the present invention, heat is added to the chamber 23 in an increasing amount until a deviation in pressure or temperature is sensed, indicating the onset of superheating. The amount of heat added is input into the microprocessor 40, along with the other pressure, temperature and flow inputs.

The operation of the steam quality sensor in the heating mode is more fully described as follows. A sample of process steam is pulled from the flow stream. The sample is then heated homogeneously until a divergence in pressure or temperature is sensed. This point of departure identifies the steam saturation condition (100% steam quality). Heating is preferably accomplished using a microprocessor control current loop, wherein the heater current is gradually increased until the point of departure of pressure or temperature is realized. Once the point of departure is sensed, the microprocessor uses the present sample flow and the wattage to calculate the enthalpy change needed to accomplish the transition from e.g., 90% quality steam to saturated steam. The enthalpy change is factored in with the process conditions (pressure and temperature) to determine the steam quality. The microprocessor then starts the process over again by decreasing the heater wattage. This hunting for the point of departure produces a reading periodically and not continuously. However, it is possible to determine steam quality several times each minute.

The steam quality sensor of the present invention possesses several advantages over prior art steam sensors. The present sensor is relatively non-intrusive because only a small sample pipe is inserted into the process steam flow. In addition, the present sensor utilizes a continuous sample steam flow instead of a grab sampling method. This allows for periodic measurement of steam quality at a higher frequency than, for example, sampling methods in which a sample of the steam is introduced into a closed chamber. Thus a method of determining steam quality several times per minute is provided.

The steam quality sensor of the present invention can be used for many purposes. For example, the performance of moisture removal equipment such as moisture separators, steam dryers, steam separators, economizers, reheaters and superheaters may be verified. Furthermore, steam enthalpy at various stages of the heat cycle may be calculated to aid in determining the thermal performance of various plant components such as turbines, heat exchangers and condensers. In particular, the steam quality sensor of the present invention may be used in a main turbine of a power generating plant to determine inlet steam conditions (Rankine cycle ratio), intermediate steam conditions (moisture separator effectiveness) and extraction steam conditions (feedwater heater performance and extraction steam system effectiveness). In addition, the quality of steam in other systems may be determined, such as feedwater heater steam space conditions, auxiliary boiler performance, steam jet performance and other turbine systems such as HPCI, RCIC and reactor feed pump turbines.

It is understood that the above description of the present invention is susceptible to considerable modifications, changes and adaptations by those skilled in the art and that such modifications, changes and adaptations are intended to be considered within the scope of the present invention, which is set forth by the appended claims. For example, while the present invention has been described in terms of measuring steam quality, the quality of other two-phase substances may also be measured in accordance with the present invention.

We Claim:

1. An apparatus for measuring steam quality comprising:
   (a) means for establishing a flow of sample steam through a chamber;
   (b) means for adding heat to or removing heat from said sample steam within said chamber;
   (c) means for detecting superheating or subcooling of said sample steam within said chamber;
   (d) means for determining the amount of heat added to or removed from said sample steam within said chamber to produce said superheating or subcooling;
   (e) means for determining the rate of steam flow through said chamber; and
   (f) means for determining the quality of said sample steam based on the amount of heat required to produce said superheating or subcooling of said sample steam and said rate of flow of said sample steam through said chamber.

2. An apparatus according to claim 1, wherein said means for establishing a flow of sample steam includes a sample pipe that extends into the flow stream of process steam to be measured.

3. An apparatus according to claim 2, wherein said sample pipe extends into substantially the middle of said flow stream.

4. An apparatus according to claim 2, wherein said means for establishing a flow of sample steam includes a condenser that produces a difference in pressure between said process steam and said condenser.

5. An apparatus according to claim 1, wherein said means for establishing a flow of sample steam includes means for producing a substantially constant rate of sample steam flow.

6. An apparatus according to claim 1, wherein said means for adding heat to said sample steam comprises an electrical resistance heater.

7. An apparatus according to claim 1, wherein said means for removing heat from said sample steam comprises a thermocouple with reversed polarity.

8. An apparatus according to claim 1, wherein said means for detecting superheating or subcooling of said sample steam comprises means for detecting a change in temperature of said sample steam.

9. An apparatus according to claim 1, wherein said means for detecting superheating or subcooling of said sample steam comprises means for detecting a change in pressure of said sample steam.

10. An apparatus according to claim 1, wherein said means for determining the rate of steam flow through said chamber comprises a mass flow meter located downstream from said chamber.

11. A method of measuring steam quality comprising the steps of:
    (a) establishing a flow of sample steam through a chamber;
    (b) adding heat to or removing heat from said sample steam within said chamber;
    (c) detecting superheating or subcooling of said sample steam within said chamber;
    (d) determining the amount of heat added to or removed from said sample steam within said chamber to produce said superheating or subcooling;
    (e) determining the rate of steam flow through said chamber; and
    (f) determining the quality of said sample steam based on the amount of heat required to produce said superheating or subcooling of said sample steam and said rate of flow of said sample steam through said chamber.

12. A method according to claim 11, wherein said flow of sample steam through said chamber is established by a sample pipe that extends into the flow stream of process steam to be measured and a condenser that produces a difference in pressure between said process steam and said condenser.

13. A method according to claim 11, wherein said flow of sample steam through said chamber is at a substantially constant rate.

14. A method according to claim 11, wherein said addition of heat to said sample steam is performed by an electrical resistance heater.

15. A method according to claim 11, wherein said removal of heat from said sample steam is performed by a thermocouple with reversed polarity.

16. A method according to claim 11, wherein said superheating or subcooling of said sample steam is detected by a change in temperature of said sample steam.

17. A method according to claim 11, wherein said superheating or subcooling of said sample steam is detected by a change in pressure of said sample steam.

18. A method according to claim 11, wherein said rate of steam flow through said chamber is determined by a mass flow meter located downstream from said chamber.

* * * * *